United States Patent
Farrugia et al.

(10) Patent No.: US 10,358,563 B2
(45) Date of Patent: Jul. 23, 2019

(54) CORE-SHELL METAL NANOPARTICLE COMPOSITE

(71) Applicant: XEROX CORPORATION, Norwalk, CT (US)

(72) Inventors: Valerie M. Farrugia, Oakville (CA); Alana Desouza, London (CA); Sandra J. Gardner, Oakville (CA)

(73) Assignee: XEROX CORPORATION, Norwalk, CT (US)

( * ) Notice: Subject to any disclaimer, the term of this patent is extended or adjusted under 35 U.S.C. 154(b) by 0 days.

(21) Appl. No.: 15/586,643

(22) Filed: May 4, 2017

(65) Prior Publication Data

US 2017/0233535 A1     Aug. 17, 2017

Related U.S. Application Data

(62) Division of application No. 14/604,598, filed on Jan. 23, 2015, now Pat. No. 9,718,970.

(51) Int. Cl.

| | | |
|---|---|---|
| *C09D 7/00* | (2018.01) | |
| *A01N 25/28* | (2006.01) | |
| *C09D 11/00* | (2014.01) | |
| *C09D 7/40* | (2018.01) | |
| *C09D 5/14* | (2006.01) | |
| *C08K 13/02* | (2006.01) | |
| *C09D 11/037* | (2014.01) | |
| *A01N 25/26* | (2006.01) | |
| *A01N 59/16* | (2006.01) | |
| *B01J 13/06* | (2006.01) | |
| *C08J 3/12* | (2006.01) | |
| *G01N 33/58* | (2006.01) | |
| *C08K 9/10* | (2006.01) | |

(52) U.S. Cl.
CPC .............. *C09D 11/00* (2013.01); *A01N 25/26* (2013.01); *A01N 25/28* (2013.01); *A01N 59/16* (2013.01); *B01J 13/06* (2013.01); *C08J 3/126* (2013.01); *C08K 13/02* (2013.01); *C09D 5/14* (2013.01); *C09D 7/70* (2018.01); *C09D 11/037* (2013.01); *G01N 33/583* (2013.01); *G01N 33/587* (2013.01); *C08J 2325/14* (2013.01); *C08J 2333/08* (2013.01); *C08J 2467/00* (2013.01); *C08K 9/10* (2013.01)

(58) Field of Classification Search
CPC ........ A01N 59/16; A01N 25/28; A01N 25/26; B01J 13/06; C08J 3/126; C09D 11/00; C09D 11/037; C09D 5/14; C09D 7/70; G01N 33/587; C08K 13/02; C08K 9/10
See application file for complete search history.

(56) References Cited

U.S. PATENT DOCUMENTS

| | | | |
|---|---|---|---|
| 5,290,654 | A | 3/1994 | Sacripante et al. |
| 5,302,486 | A | 4/1994 | Patel et al. |
| 5,418,108 | A | 5/1995 | Kmiecik-Lawrynowicz et al. |
| 7,312,011 | B2 | 12/2007 | Patel et al. |
| 7,820,737 | B2 | 10/2010 | Kumacheva |
| 7,892,714 | B2 | 2/2011 | McDougall et al. |
| 7,935,540 | B2 | 5/2011 | Kalgutkar et al. |
| 7,939,237 | B2 | 5/2011 | McDougall et al. |
| 8,383,311 | B2 | 2/2013 | Cheng et al. |
| 2004/0247690 | A1 | 12/2004 | Yang |
| 2006/0083694 | A1 | 4/2006 | Kodas et al. |
| 2009/0130778 | A1 | 5/2009 | Kalgutkar et al. |
| 2012/0202148 | A1 | 8/2012 | Veregin et al. |
| 2013/0259808 | A1 | 10/2013 | Chen et al. |
| 2017/0037234 | A1 | 2/2017 | Prud'Homme et al. |

OTHER PUBLICATIONS

Lopez-Tobar, Eduardo, Stability of the Disulfide Bond in Cystine Adsorbed on Silver and Gold Nanoparticles as Evidenced by SERS Data, J. Phys. Chem, C2013, 117, 1531-1537.
Sironmani, A. et al. "Silver Nanoparticles—Universal Multifunctional Nanoparticles for Biosensing, Imaging for Diagnostics and Targeted Drug Delivery for Therapeutic Applications", 2011, 463-488 ; in the book: Drug discovery and development—present and future.
Kneipp, K. et al. Surface-enhanced Raman scattering and biophysics, J. Phys.: Condens. Matter 14 (2002) R597-R624.
Lee, K et al., In Vivo Imaging of Transport and Biocompatibility of Single Silver Nanoparticles in Early Development of Zebrafish Embryos (Sep. 2007) ACS Nano, vol. 1, No. 2, 133-143
Korbekandi, H. et al., "Silver Nanoparticles", The Delivery of Nanoparticles, 2012, 3-36.
Rashid, M. et al. Synthesis of Silver Nano Particles (Ag-NPs) and their uses for Quantitative Analysis of Vitamin C Tablets, Dhaka Univ. J. Pharm. Sci. 12(1): 29-33, Jun. 2013.
Rivera, P. et al., "Synthesis and characterization of silver nanoparticles for biosensor design", Universidad Interamericana de Puerto Rico—Recinto de Ponce, Revista 360° /No. 8, 2013, 1-8.

*Primary Examiner* — Robert A Wax
*Assistant Examiner* — Olga V. Tcherkasskaya
(74) *Attorney, Agent, or Firm* — Pillsbury Winthrop Shaw Pittman LLP

(57) ABSTRACT

A nanocomposite includes a core comprising a first polymer, a shell disposed about the core, the shell comprising a sulfonated polyester, the first polymer and sulfonated polyester are different, and a plurality of silver nanoparticles disposed throughout the shell layer.

5 Claims, 12 Drawing Sheets

CORE-SHELL METAL NANOPARTICLE COMPOSITE

CROSS-REFERENCE TO RELATED APPLICATIONS

This application is a divisional application of co-pending U.S. patent application Ser. No. 14/604,598, filed Jan. 23, 2015, which is herein incorporated by reference in its entirety.

BACKGROUND

The present disclosure relates to composite materials. In particular, embodiments herein relate to core-shell nanocomposites comprising mixed organic-inorganic components.

Organic/inorganic nanocomposites are materials made up of organic polymers embedded with inorganic nanoscale fillers. The benefit of combining inorganic nanofillers within organic polymers is that the resultant composite becomes more rigid, thermally stable and displays other unique properties not seen with organic polymers alone. The polymer itself confers processability to the composite and imparts flexibility, improves dielectric properties and is ductile. The nanofillers provide a significant increase in interfacial area which creates a significant volume fraction of interfacial polymer with properties different from the bulk polymer, even at low loadings. The physical properties of the inorganic nanoparticles, in particular, can be enhanced by encapsulating or embedding within a polymer.

There is a growing interest in embedding nanometals into polymer matrices due to the potential applications that are possible. By combining the properties from both inorganic (i.e., silver, gold, copper, etc.) and organic (polymer) systems, many new products can be created. Areas of growth with regard to silver nanoparticles (AgNPs) include, without limitation, antimicrobial applications, biosensor materials, composite fibers, cryogenic superconducting materials, cosmetic products, and electronic components. The unique properties (e.g., size and shape dependent optical, electrical, and magnetic properties) of silver nanoparticles, in particular, have resulted in their increased use in number of consumer and medical products. Methods such as three dimensional (3D) printing and ink jet deposition can be used to transfer the functional core-shell organic/inorganic nanocomposites disclosed herein to a substrate of choice. Other areas of application include, for example, aqueous ink formulations for sensor and antimicrobial applications.

Most methods for silver/polymer nanostructured materials require that the silver salt precursor is reduced in a chemical reaction prior to incorporation into polymer matrices. The most widely used silver ion precursor for the synthesis of AgNPs is silver nitrate ($AgNO_3$). The most readily used reducing agents for the synthesis of AgNPs are sodium borohydride or sodium citrate. The most common stabilizing agents for nanosilver are citrate and PVP (polyvinylpyrrolidone).

Conventional methods for making silver/polymer nanostructured materials generally require the melt mixing or extrusion of AgNPs in polymer matrixes which lead to aggregated silver particles. Other methods use in situ synthesis of metal nanoparticles in polymer matrixes which involves the dissolution and reduction of metal salts and/or simultaneously with polymer synthesis. The polymer matrix has a role in keeping the AgNPs dispersed as well as maintaining overall chemical and mechanical stability.

Methods for the synthesis of core-shell or hybrid colloid dispersions currently lack control of morphology and colloidal properties are generally inferior. It has also been found that most conventional methods require filtration, sedimentation, and centrifugation processes, which are challenging and time consuming. The development of processes for the synthesis of core-shell organic/inorganic nanoparticles with precise positioning of the silver nanoparticles at the surface of the nanoparticle, as disclosed herein, provides reactive or stimuli-responsive colloidal particles that also have a well-defined structure, homogeneous encapsulation and well-defined morphology. Other issues that arise in conventional methods which are overcome by the methods herein include incompatibility between the polymer and inorganic material especially when highly hydrophobic monomers are used in any polymerization stage of the process. In these cases surface modification or treatment of the inorganic nanoparticles are usually employed to make the nanoparticles compatible and thus dispersible within the organic polymer matrix.

Finally, it is known that uncoated silver nanoparticles can be toxic but when protected by an organic layer or embedded within an organic matrix they become less toxic or in other words biocompatible.

SUMMARY

In some aspects, embodiments herein relate to nanocomposites comprising a core comprising a first polymer, a shell disposed about the core, the shell comprising a sulfonated polyester, wherein the first polymer and sulfonated polyester are different; and a plurality of silver nanoparticles disposed throughout the shell layer.

In some aspects, embodiments herein relate to methods of making a core-shell nanocomposite comprising heating a sulfonated polyester resin in water at a temperature from about 65° C. to 90° C., adding aqueous solution of silver (I) ion source dropwise to the heated sulfonated polyester form an emulsion, optionally adding an aqueous solution of a reducing agent dropwise to the emulsion, and adding the emulsion dropwise to polystyrene-co-n-butyl acrylate latex nanoparticles in water, continuing heating to form the core-shell nanocomposite.

In some aspects, embodiments herein relate to articles comprising the aforementioned nanocomposites.

BRIEF DESCRIPTION OF DRAWINGS

Various embodiments of the present disclosure will be described herein below with reference to the figures wherein.

DETAILED DESCRIPTION

Figure 1:
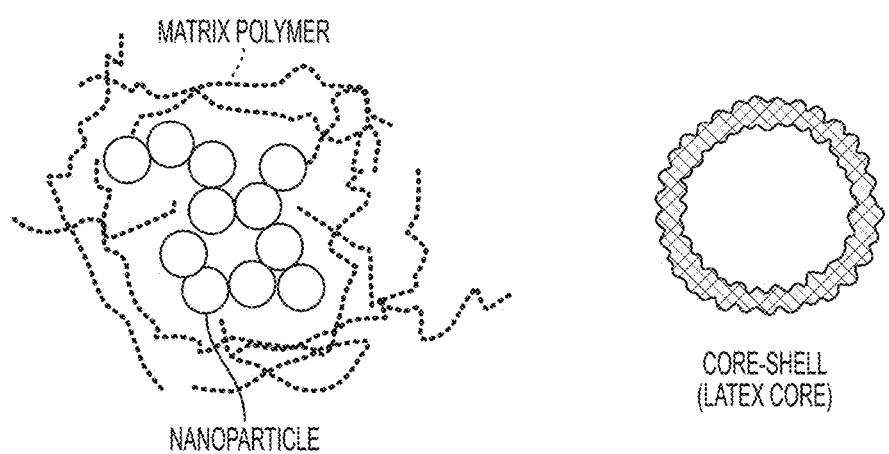
FIG. 1 shows (left) an illustration of silver nanoparticles dispersed throughout a sulfonated polymer matrix which constitutes the shell material; (right) shows core-shell structure of nanocomposites, in accordance with embodiments herein.

Core-shell nanoparticles have been reported throughout literature as functional composites for many device applications related to biomedical, enhancing photoluminescence, pharmaceutical applications, catalysis, creating photonic crystals and electronics. As well, these core-shell materials are economically sound since the bulk or core is mainly organic while the shell contains organic with the more expensive precious metals such as gold and silver.

Embodiments provide for the preparation and characterization of core-shell nanocomposites that selectively immobilize silver nanoparticles in the outer shell layer of the core-shell nanoparticles. The present methods disclosed herein are environmentally friendly processes for synthesizing silver nanoparticles that do not require the use of toxic chemicals. Methods herein provide green chemistry and biocompatibility in preparing hybrid organic/inorganic nanocomposites. The hybrid nanocomposites have the ability to take on inorganic characteristics related to coating performance (such as robustness) and thermal stability. Deliberate placement of the silver nanoparticles (AgNPs) in the shell provides easy accessibility of the silver for sensor or antimicrobial applications.

As demonstrated below in the Examples, polystyrene-co-n-butyl acrylate (PSnBA) nanoparticles (i.e., emulsion aggregation toner latex) were coated with a sulfonated polyester shell that was initially self-dispersed while simultaneously reducing silver nitrate to AgNPs. The polystyrene-co-n-butyl acrylate nanoparticles were used as templates in water which were coated in situ with the silver-containing sulfonated polyester via attractive electrostatic interaction or by specific interactions (e.g. ion pairing, complexation, dipole-dipole, etc.). The addition of an incompatible polymer such as sulfonated polyester with inorganic features (i.e., silver nanoparticles) to the PSnBA core provides highly functional core-shell nanoparticles. Embodiments herein operate with aqueous systems and waterborne dispersions which are environmentally sound and possibly the route-of-choice for any future development of large scale materials/applications. The methods require minimal time to synthesize these polymer metal nanocomposites Embodiments herein provide polymeric core-shell metal-containing nanocomposites and an environmentally friendly methods (green chemistry) to synthesize them. Although embodiments herein focus on exemplary silver nanoparticles as part of the composite, those skilled in the art will recognize the ability to use other metals in shell coating of the nanocomposites herein including, without limitation, gold, platinum, copper, nickel and palladium.

In embodiments, two very different polymeric materials can be used to prepare the core-shell nanocomposites herein. The core may be made up of emulsion polymerization (EP) polystyrene-n-butyl acrylate (PSnBA) latex particles. These stable monodispersed EP emulsion nanoparticles were used as templates (or the core) for a silver nanoparticle/polyester coating (shell). The shell polymer is generally made up of metal sulfonated polyester (SPE) polymer. Without being bound by theory, the sulfonated polymer self-assembles in water at about 90° C. where the hydrophobic backbone forms the core of the sphere, while the hydrophilic sulfonate functional groups are oriented to face the surrounding water. When silver is added, the electrostatic attraction between the sulfonate groups and the Ag+ ions causes an association between the silver and the polymer matrix. A reducing agent can be optionally added to facilitate the reduction of Ag+ to Ag(0) on the surface of SPE (branched sulfonated polyester (BSPE) polymer was used in the Examples herein). Advantageously, the branched structure of the SPE creates a porous structure that allows for diffusion of materials through it.

The silver nanoparticles are embedded within the BSPE matrix polymer as seen in FIG. 1 (left schematic) which is then coated onto a poly(styrene-co-nbutyl acrylate) latex core as seen in FIG. 1 (right schematic).

Figure 2:
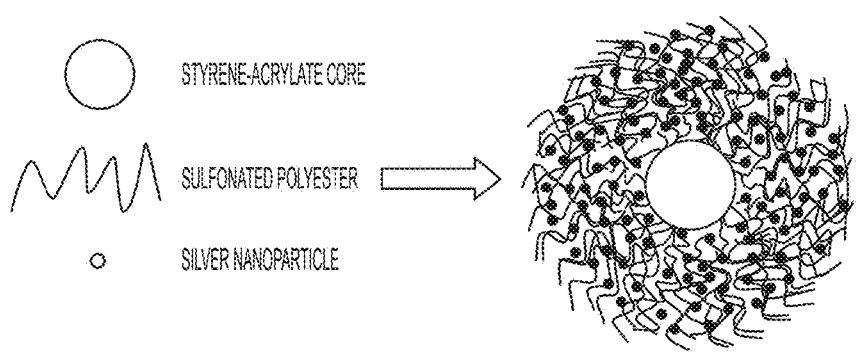
FIG. 2 shows another illustration of a nanocomposite, in accordance with embodiments herein.
Figure 3:
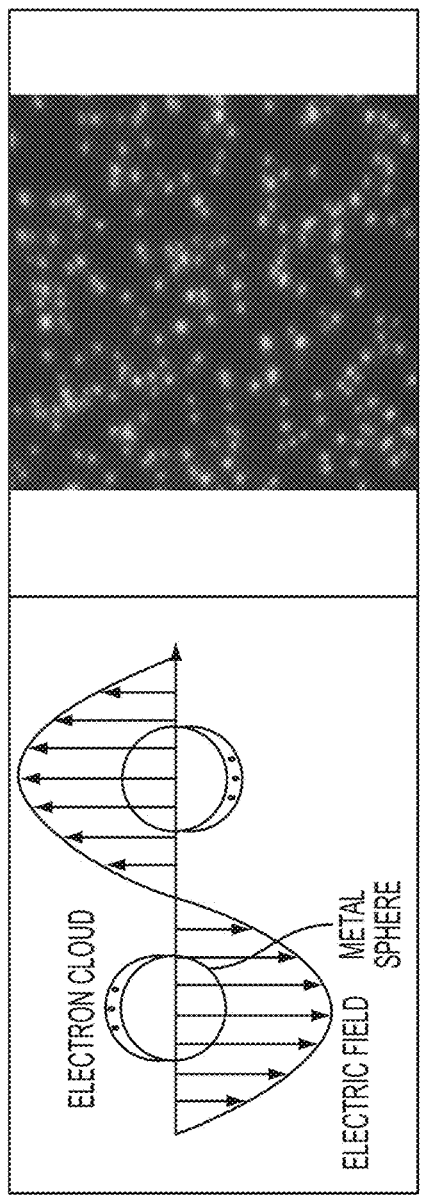
FIG. 3 shows an illustration of the optical properties of noble metal nanoparticles.
Figure 4A:
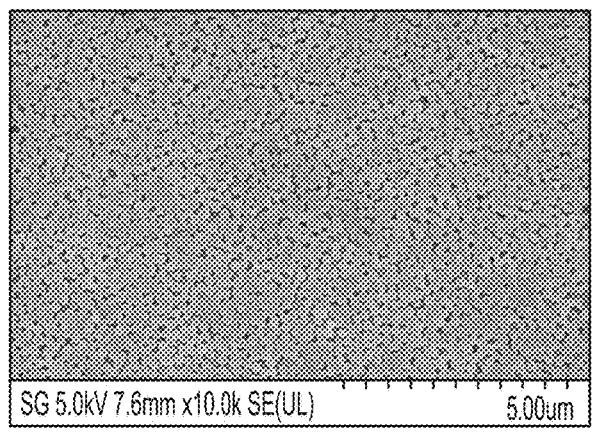
FIGS. 4A-C show scanning electron microscope (SEM) images of styrene-acrylate particles at various magnifications.
Figure 4B:
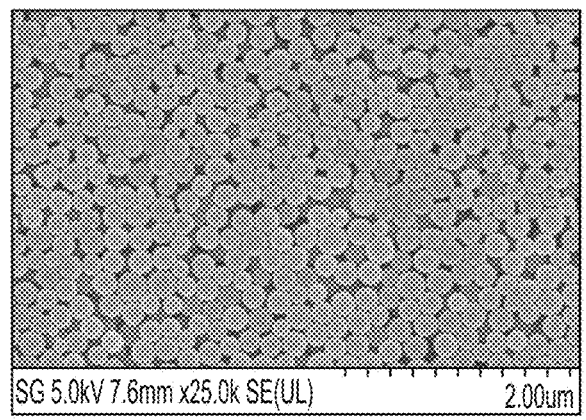
Figure 4C:
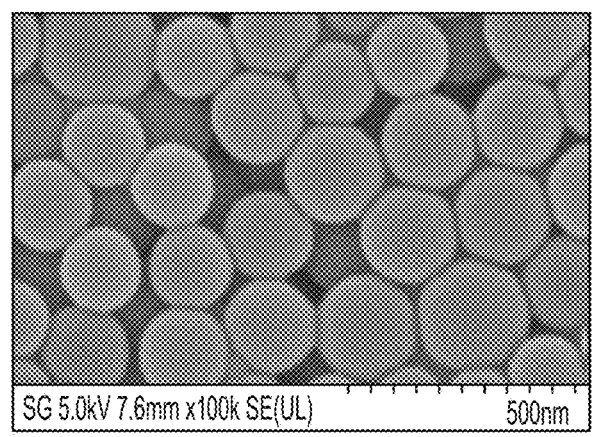
Figure 5A:
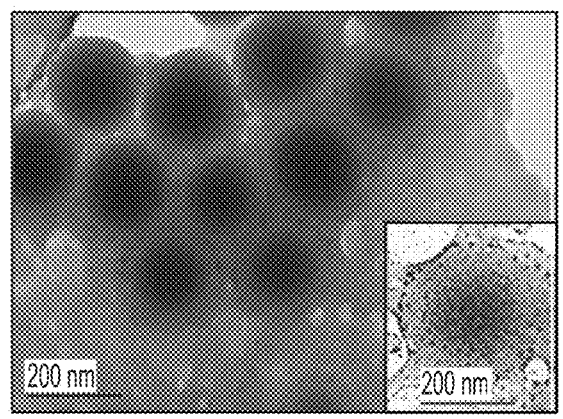
FIGS. 5A-C show (A) and (B) transmission electron microscope (TEM) images of poly(stryrene)-co-n-butyl acrylate) with sulfonated polyester-silver nanoparticle shell coating at different magnification; the images indicate good dispersion of silver nanoparticles; (C) SEM of the sample.
Figure 5B:
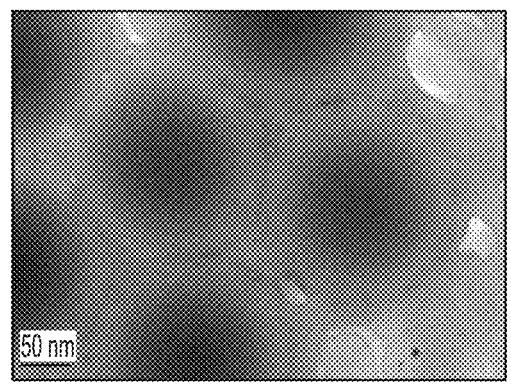
Figure 5C:
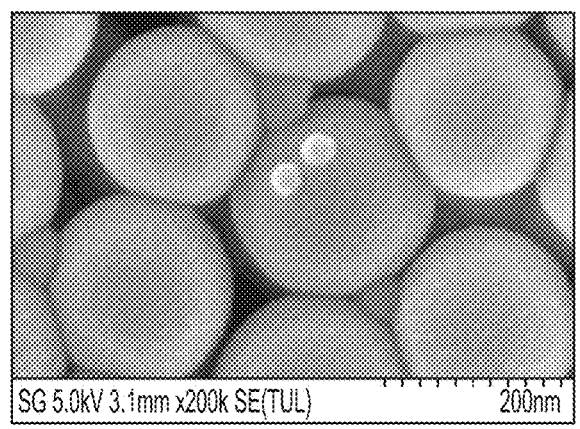
Figure 6:
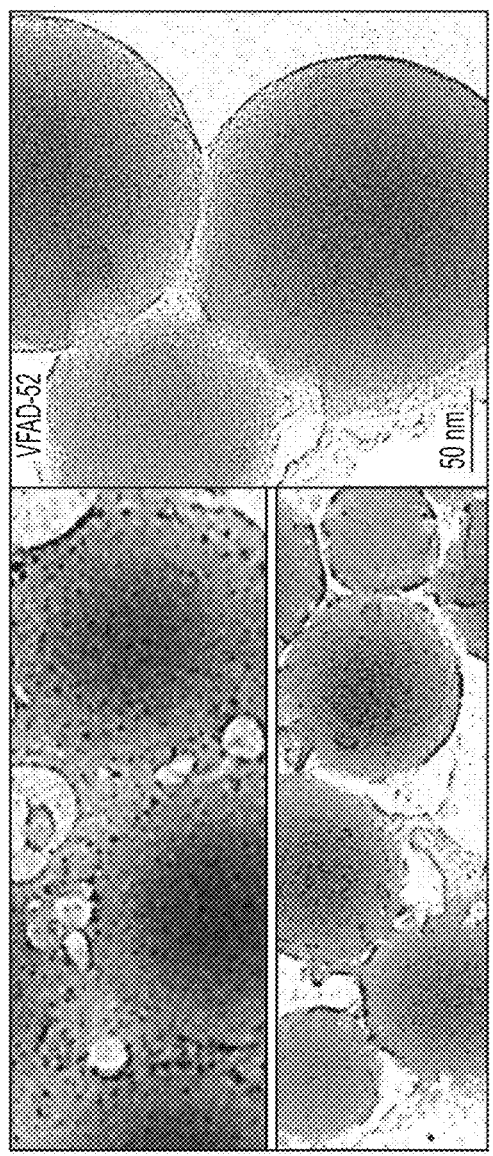
FIG. 6 shows further TEM images of the sample of FIGS. 5A-C.
Figure 7:
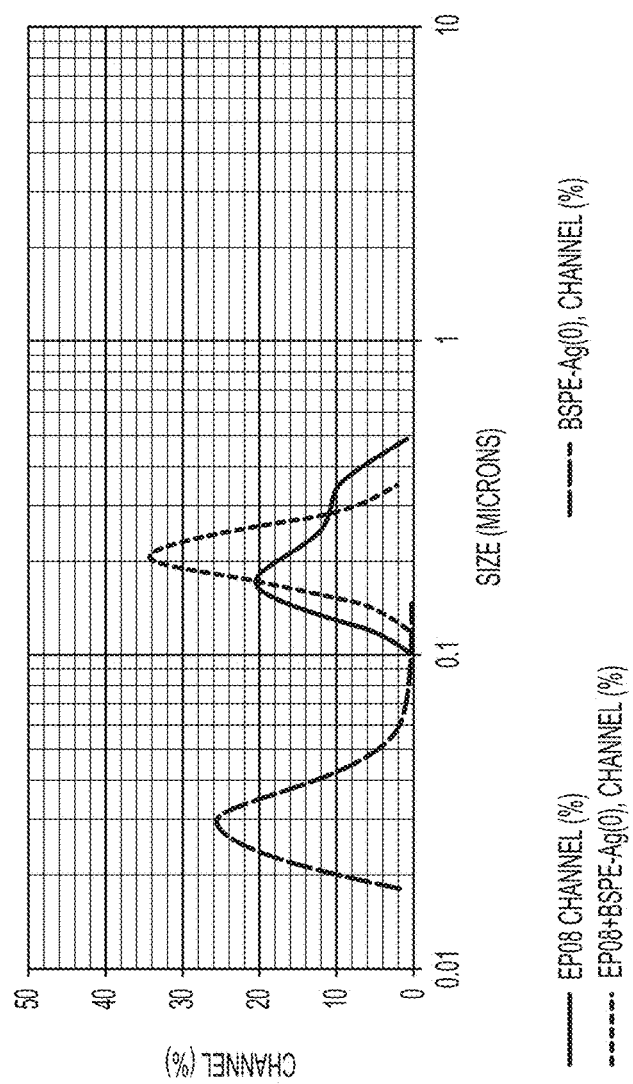
FIG. 7 shows an overlay plot of particle size distributions for styrene acrylate alone, silver nanoparticle-sulfonated polyester composite alone; and the core-shell structure.
Figure 8:
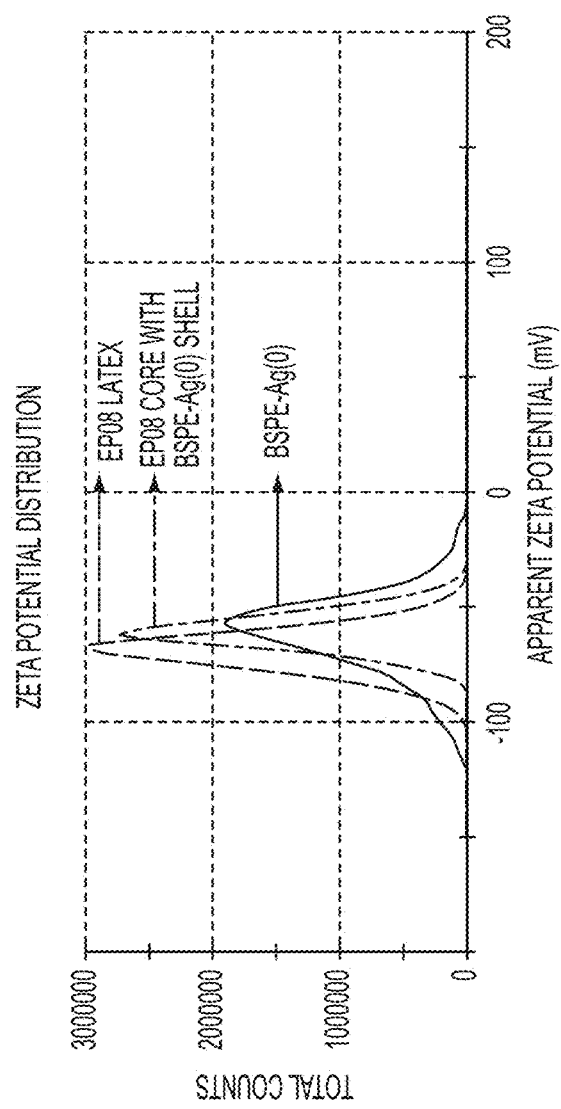
FIG. 8 shows an overlay plot of zeta potential distribution for styrene acrylate alone, silver nanoparticle-sulfonated polyester composite alone; and the core-shell structure.

FIG. 2 shows a schematic of the overall core-shell structure which selectively immobilizes AgNPs in the outer shell layer of the core-shell nanoparticles. This makes them easily accessible for many functional applications.

The synthesis of core-shell nanoparticles involves three steps which are all aqueous-based. Step 1 is to synthesize the core (if non-toner latex is required), step 2 is to dissipate the BSPE during the reduction of silver nitrate and step 3 is to coat the core with the shell component. The organic core is synthesized via emulsion polymerization. The organic core is then coated with the inorganic/organic polymer shell "in situ".

The end product is tailor-made materials that have an amphiphilic organic-inorganic shell containing reduced silver (Ag0) and an organic core which plays the part of a template for the adsorption of the nanocomposite shell which is controlled by attractive electrostatic interaction or by specific interactions (e.g. ion pairing, complexation, dipole-dipole, etc.).

These core-shell organic/inorganic nanocomposite particles can be used for a wide range of applications that require silver nanoparticles to be localized on the surface of a particle such as sensors or antimicrobial coatings. Another feature of these core-shell nanocomposites is that the BSPE/AgNP shell possesses the plasmonic properties required for the sensing applications which can be applied to imaging material, such as toner or ink. The surface plasmon resonance (SPR) properties of silver utilize changes in the refractive index at the sensor/fluid interface to detect analyte molecules. Using this approach to design AgNP core-shell nanoparticles result in a simple, quick and inexpensive method for preparing metal/organic nanoparticles. These nanoparticles can be used for the detection of many types of analytes (e.g., Cu, Cr) or biomolecules such as streptavidin molecules.

These and other advantages will be apparent to those skilled in the art.

In embodiments, there are provided nanocomposites comprising: a core comprising a first polymer, a shell disposed about the core, the shell comprising a sulfonated polyester; wherein the first polymer and sulfonated polyester are different, and a plurality of silver nanoparticles disposed throughout the shell layer.

In embodiments, the nanocomposite has an effective diameter in a range from about 25 nm to about 500 nm, or about 50 nm to about 400 nm or about 100 to about 250 nm.

In embodiments, the core is part of an emulsion of the first polymer, the first polymer comprising one or more monomer units selected from the group consisting of styrene, n-butyl acrylate, methacrylic acid, and beta-carboxyethyl acrylate (β-CEA). In embodiments, the first polymer is polystyrene-co-n-butyl acrylate (PSnBA). Examples of resins or polymers useful as core first polymer include, without limitation, one or more of poly(styrene-butadiene), poly(para-methyl styrene-butadiene), poly(meta-methyl styrene-butadiene), poly(alpha-methyl styrene-butadiene), poly(methylmethacrylate-butadiene), poly(ethylmethacrylate-butadiene), poly(propylmethacrylate-butadiene), poly(butylmethacrylate-butadiene), poly(methylacrylate-butadiene), poly(ethylacrylate-butadiene), poly(propylacrylate-butadiene), poly(butylacrylate-butadiene), poly(styrene-isoprene), poly(para-methyl styrene-isoprene), poly(metamethyl styrene-isoprene), poly(alpha-methylstyrene-isoprene), poly(methylmethacrylate-isoprene), poly(ethylmethacrylate-isoprene), poly(propylmethacrylate-isoprene), poly(butylmethacrylate-isoprene), poly(methylacrylate-isoprene), poly(ethylacrylate-isoprene), poly(propylacrylate-isoprene), and poly(butylacrylate-isoprene); polymers such as poly(styrene-butadiene-acrylic acid), poly(styrene-butadiene-methacrylic acid), polyethylene-terephthalate, polypropylene-terephthalate, polybutylene-terephthalate, polypentylene-terephthalate, polyhexalene-terephthalate, polyheptadene-terephthalate, polyoctalene-terephthalate and the like. The resin selected, which generally can be in embodiments styrene acrylates, styrene butadienes, styrene methacrylates, or polyesters.

Exemplary polymers includes styrene acrylates, styrene butadienes, styrene methacrylates, and more specifically, poly(styrene-alkyl acrylate), poly(styrene-1,3-diene), poly(styrene-alkyl methacrylate), poly (styrene-alkyl acrylate-acrylic acid), poly(styrene-1,3-diene-acrylic acid), poly (styrene-alkyl methacrylate-acrylic acid), poly(alkyl methacrylate-alkyl acrylate), poly(alkyl methacrylate-aryl acrylate), poly(aryl methacrylate-alkyl acrylate), poly(alkyl methacrylate-acrylic acid), poly(styrene-alkyl acrylate-acrylonitrile-acrylic acid), poly (styrene-1,3-diene-acrylonitrile-acrylic acid), poly(alkyl acrylate-acrylonitrile-acrylic acid), poly(styrene-butadiene), poly(methylstyrene-butadiene), poly(methyl methacrylate-butadiene), poly(ethyl methacrylate-butadiene), poly(propyl methacrylate-butadiene), poly(butyl methacrylate-butadiene), poly(methyl acrylate-butadiene), poly(ethyl acrylate-butadiene), poly(propyl acrylate-butadiene), poly(butyl acrylate-butadiene), poly(styrene-isoprene), poly(methylstyrene-isoprene), poly (methyl methacrylate-isoprene), poly(ethyl methacrylate-isoprene), poly(propyl methacrylate-isoprene), poly(butyl methacrylate-isoprene), poly(methyl acrylate-isoprene), poly(ethyl acrylate-isoprene), poly(propyl acrylate-isoprene), poly(butyl acrylate-isoprene), poly(styrene-propyl acrylate), poly(styrene-butyl acrylate), poly (styrene-butadiene-acrylic acid), poly(styrene-butadiene-methacrylic acid), poly (styrene-butadiene-acrylonitrile-acrylic acid), poly(styrene-butyl acrylate-acrylic acid), poly(styrene-butyl acrylate-methacrylic acid), poly(styrene-butyl acrylate-acrylononitrile), poly(styrene-butyl acrylate-acrylonitrile-acrylic acid), poly(styrene-butadiene), poly(styrene-isoprene), poly(styrene-butyl methacrylate), poly(styrene-butyl acrylate-acrylic acid), poly(styrene-butyl methacrylate-acrylic acid), poly(butyl methacrylate-butyl acrylate), poly(butyl methacrylate-acrylic acid), poly(acrylonitrile-butyl acrylate-acrylic acid), and combinations thereof. In embodiments, the polymer is poly(styrene/butyl acrylate/beta carboxyl ethyl acrylate). The polymer may be block, random, or alternating copolymers.

In embodiments, a gel latex may be added to the core latex resin. A gel latex may refer, in embodiments, to a crosslinked resin or polymer, or mixtures thereof. In embodiments, the gel latex may be a mixture of a crosslinked resin and a non-crosslinked resin. Non-crosslinked resin particles may be composed of any of the latex resins or polymers described above.

The gel latex may include, for example, submicron crosslinked resin particles having a size of, for example, from about 10 nanometers to about 400 nanometers, and in embodiments from about 20 to 200 nanometers in volume average diameter. The gel latex may be suspended in an aqueous phase of water containing a surfactant.

The surfactant is selected in an amount from about 0.5 percent by weight to about 5 percent by weight of the solids, and in embodiments from about 0.7 percent by weight to about 2 percent by weight of the solids.

The crosslinked resin may be a crosslinked polymer such as crosslinked styrene acrylates, styrene butadienes, and/or styrene methacrylates. In particular, exemplary crosslinked resins are crosslinked poly(styrene-alkyl acrylate), poly(styrene-butadiene), poly(styrene-isoprene), poly(styrene-alkyl methacrylate), poly(styrene-alkyl acrylate-acrylic acid), poly(styrene-butadiene-acrylic acid), poly(styrene-isoprene-acrylic acid), poly (styrenealkyl methacrylate-acrylic acid), poly(alkyl methacrylate-alkyl acrylate), poly (alkyl methacrylate-aryl acrylate), poly(aryl methacrylate-alkyl acrylate), poly(alkyl methacrylate-acrylic acid), poly(styrene-alkyl acrylate-acrylonitrile acrylic acid), crosslinked poly (alkyl acrylate-acrylonitrile-acrylic acid), and mixtures thereof.

A crosslinker, such as divinyl benzene or other divinyl aromatic or divinyl acrylate or methacrylate monomers may be used in the crosslinked resin. The crosslinker may be present in an amount of from about 0.01 percent by weight to about 25 percent by weight, and in embodiments of from about 0.5 percent by weight to about 15 percent by weight of the crosslinked resin.

In embodiments, the sulfonated polyester is branched. In embodiments, the sulfonated polyester is linear. In embodiments, the sulfonated polyester is a sodium, potassium or lithium salt of a polymer selected from the group consisting of poly(1,2-propylene-5-sulfoisophthalate), poly(neopentylene-5-sulfoisophthalate), poly(diethylene-5-sulfoisophthalate), copoly-(1,2-propylene-5-sulfoisophthalate)-copoly-(1,2-propylene-terephthalatephthalate), copoly-(1,2 propylenediethylene5-sulfoisophthalate)-copoly-(1,2-propylene-diethylene-terephthalatephthalate) copoly(ethylene neopentylene-5-sulfoiso-phthalate)-copoly(ethylene-neopentylene-terephthalatephthalate), and copoly(propoxylated bisphenol A)-copoly-(propoxylated bisphenol A-5-sulfoisophthalate).

In embodiments, the sulfonated polyester resin is a branched polymer. In embodiments, the sulfonated polyester resin is a linear polymer. In embodiments, the sulfonated polyester matrix is a lithium, potassium, or sodium salt of a polymer selected from the group consisting of poly(1,2-propylene-5-sulfoisophthalate), poly(neopentylene-5-sulfoisophthalate), poly(diethylene-5-sulfoisophthalate), copoly-(1,2-propylene-5-sulfoisophthalate)-copoly-(1,2-propylene-terphthalate), copoly-(1,2-propylenediethylene-5-sulfoisophthalate)-copoly-(1,2-propylene-diethylene-terephthalatephthalate), copoly(ethylene-neopentylene-5-sulfoisophthalate)-copoly-(ethylene-neopentylene-terephthalatephthalate), and copoly(propoxylated bisphenol A)-copoly-(propoxylated bisphenol A-5-sulfoisophthalate).

In embodiments, the sulfonated polyester resin comprises a polyol monomer unit selected from the group consisting of trimethylolpropane, 1,2-propanediol, diethylene glycol, and combinations thereof.

In embodiments, the sulfonated polyester resin comprises a diacid monomer unit selected from the group consisting of terephthalic acid, sulfonated isophthalic acid, and combinations thereof.

In general, the sulfonated polyesters may have the following general structure, or random copolymers thereof in which the n and p segments are separated.

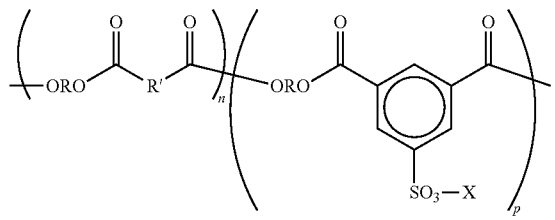

wherein R is an alkylene of, for example, from 2 to about 25 carbon atoms such as ethylene, propylene, butylene, oxyalkylene diethyleneoxide, and the like; R' is an arylene of, for example, from about 6 to about 36 carbon atoms, such as a benzylene, bisphenylene, bis(alkyloxy) bisphenolene, and the like; and p and n represent the number of randomly repeating segments, such as for example from about 10 to about 100,000.

Examples further include those disclosed in U.S. Pat. No. 7,312,011 which is incorporated herein by reference in its entirety. Specific examples of amorphous alkali sulfonated polyester based resins include, but are not limited to, copoly(ethylene-terephthalate)-copoly-(ethylene-5-sulfo-isophthalate), copoly(propylene-terephthalate)-copoly(propylene-5-sulfo-isophthalate), copoly(diethylene-terephthalate)-copoly(diethylene-5-sulfo-isophthalate), copoly(propylene-diethylene-terephthalate)-copoly(propylene-diethylene-5-sulfo-isophthalate), copoly(propylene-butylene-terephthalate)-copoly(propylene-butylene-5-sulfo-isophthalate), copoly(propoxylated bisphenol-A-fumarate)-copoly(propoxylated bisphenol A-5-sulfo-isophthalate), copoly(ethoxylated bisphenol-A-fumarate)-copoly(ethoxylated bisphenol-A-5-sulfo-isophthalate), and copoly(ethoxylated bisphenol-A-maleate)-copoly(ethoxylated bisphenol-A-5-sulfo-isophthalate), and wherein the alkali metal is, for example, a sodium, lithium or potassium ion. Examples of crystalline alkali sulfonated polyester based resins alkali copoly(5-sulfoisophthaloyl)-co-poly(ethylene-adipate), alkali copoly(5-sulfoisophthaloyl)-copoly(propylene-adipate), alkali copoly(5-sulfoisophthaloyl)-copoly(butylene-adipate), alkali copoly(5-sulfo-isophthaloyl)-copoly(pentylene-adipate), and alkali copoly(5-sulfo-iosphthalbyl)-copoly(octylene-adipate), alkali copoly(5-sulfo-isophthaloyl)-copoly(ethylene-adipate), alkali copoly(5-sulfo-isophthaloyl)-copoly (propylene-adipate), alkali copoly(5-sulfo-isophthaloyl)-co-poly(butylene-adipate), alkali copoly(5-sulfo-isophthaloyl)-copoly(pentylene-adipate), alkali copoly(5-sulfo-isophthaloyl)-copoly(hexylene-adipate), alkali copoly(5-sulfo-isophthaloyl)-copoly(octylene-adipate), alkali copoly(5-sulfoisophthaloyl)-copoly(ethylene-succinate), alkali copoly(5-sulfoisophthaloyl-copoly(butylene-succinate), alkali copoly(5-sulfoisophthaloyl)-copoly(hexylene-succinate), alkali copoly(5-sulfoisophthaloyl)-copoly(octylene-succinate), alkali copoly(5-sulfo-isophthaloyl)-copoly(ethylene-sebacate), alkali copoly(5-sulfo-isophthaloyl)-copoly(propylene-sebacate), alkali copoly(5-sulfo-isophthaloyl)-copoly(butylene-sebacate), alkali copoly(5-sulfo-isophthaloyl)-copoly(pentylene-sebacate), alkali copoly(5-sulfo-isophthaloyl)-copoly(hexylene-sebacate), alkali copoly(5-sulfo-isophthaloyl)-copoly(octylene-sebacate), alkali copoly(5-sulfo-isophthaloyl)-copoly(ethylene-adipate), alkali copoly(5-sulfo-isophthaloyl)-copoly(propylene-adipate), alkali copoly(5-sulfo-iosphthaloyl)-copoly(butylene-adipate), alkali copoly(5-sulfo-isophthaloyl)-copoly(pentylene-adipate), alkali copoly(5-sulfo-isophthaloyl)copoly(hexylene-adipate), poly(octylene-adipate), and wherein the alkali is a metal like sodium, lithium or potassium. In embodiments, the alkali metal is lithium. In embodiments, the alkali metal is sodium.

The linear amorphous polyester resins are generally prepared by the polycondensation of an organic diol and a diacid or diester, at least one of which is sulfonated or a sulfonated difunctional monomer being included in the reaction, and a polycondensation catalyst. For the branched amorphous sulfonated polyester resin, the same materials may be used, with the further inclusion of a branching agent such as a multivalent polyacid or polyol.

Examples of diacid or diesters selected for the preparation of amorphous polyesters include dicarboxylic acids or diesters selected from the group consisting of terephthalic acid, phthalic acid, isophthalic acid, fumaric acid, maleic acid, itaconic acid, succinic acid, succinic anhydride, dodecylsuccinic acid, dodecylsuccinic anhydride, glutaric acid, glutaric anhydride, adipic acid, pimelic acid, suberic acid, azelic acid, dodecanediacid, dimethyl terephthalate, diethyl terephthalate, dimethylisophthalate, diethylisophthalate, dimethylphthalate, phthalic anhydride, diethylphthalate, dimethylsuccinate, dimethylfumarate, dimethylmaleate, dimethylglutarate, dimethyladipate, dimethyl dodecylsuccinate, and mixtures thereof. The organic diacid or diester are selected, for example, from about 45 to about 52 mole percent of the resin. Examples of diols utilized in generating the amorphous polyester include 1,2-propanediol, 1,3-propanediol, 1,2-butanediol, 1,3-butanediol, 1,4-butanediol, pentanediol, hexanediol, 2,2-dimethylpropanediol, 2,2,3-trimethylhexanediol, heptanediol, dodecanediol, bis(hyroxyethyl)-bisphenol A, bis(2-hyroxypropyl)-bisphenol A, 1,4-cyclohexanedimethanol, 1,3-cyclohexanedimethanol, xylenedimethanol, cyclohexanediol, diethylene glycol, bis (2-hydroxyethyl) oxide, dipropylene glycol, dibutylene, and mixtures thereof. The amount of organic diol selected can vary, and more specifically, is, for example, from about 45 to about 52 mole percent of the resin.

Alkali sulfonated difunctional monomer examples, wherein the alkali is lithium, sodium, or potassium, include dimethyl-5-sulfo-isophthalate, dialkyl-5-sulfo-isophthalate-4-sulfo-1,8-naphthalic anhydride, 4-sulfo-phthalic acid, 4-sulfophenyl-3,5-dicarbomethoxybenzene, 6-sulfo-2-naphthyl-3,5-dicarbomethoxybenzene, sulfo-terephthalic acid, dimethyl-sulfo-terephthalate, dialkyl-sulfo-terephthalate, sulfo-ethanediol, 2-sulfo-propanediol, 2-sulfo-butanediol, 3-sulfo-pentanediol, 2-sulfo-hexanediol, 3-sulfo-2-methylpentanediol, N,N-bis(2-hydroxyethyl)-2-aminoethane sulfonate, 2-sulfo-3,3-dimethylpent-anediol, sulfo-p-hydroxybenzoic acid, mixtures thereto, and the like. Effective difunctional monomer amounts of, for example, from about 0.1 to about 2 weight percent of the resin can be selected.

Branching agents for use in forming the branched amorphous sulfonated polyester include, for example, a multivalent polyacid such as 1,2,4-benzene-tricarboxylic acid, 1,2, 4-cyclohexanetricarboxylic acid, 2,5,7-naphthalenetricarboxylic acid, 1,2,4-naphthalenetricarboxylic acid, 1,2,5-hexanetricarboxylic acid, 1,3-dicarboxyl-2-methyl-2-methylene-carboxylpropane, tetra(methylene-carboxyl)methane, and 1,2,7,8-octanetetracarboxylic acid, acid anhydrides thereof, and lower alkyl esters thereof, 1 to about 6 carbon atoms; a multivalent polyol such as sorbitol, 1,2,3,6-hexanetetrol, 1,4-sorbitane, pentaerythritol, dipentaerythritol, tripentaerythritol, sucrose, 1,2,4-butanetriol, 1,2,5-pentatriol, glycerol, 2-methylpropanetriol, 2-methyl-1,2,4-butanetriol, trimethylolethane, trimethylolpropane, 1,3,5-trihydroxymethylbenzene, mixtures thereof, and the like. The branching agent amount selected is, for example, from about 0.1 mole percent to about 5 mole percent of the resin.

Polycondensation catalyst examples for amorphous polyesters include tetraalkyl titanates, dialkyltin oxide such as dibutyltin oxide, tetraalkyltin such as dibutyltin dilaurate, dialkyltin oxide hydroxide such as butyltin oxide hydroxide, aluminum alkoxides, alkyl zinc, dialkyl zinc, zinc oxide, stannous oxide, or mixtures thereof; and which catalysts are selected in amounts of, for example, from about 0.01 mole percent to about 5 mole percent based on the starting diacid or diester used to generate the polyester resin.

In embodiments, the silver nanoparticles that serve as the building blocks for the silver nanodendrites may comprise solely elemental silver or may be a silver composite, including composites with other metals. Such metal-silver composite may include either or both of (i) one or more other metals and (ii) one or more non-metals. Suitable other metals include for example Al, Au, Pt, Pd, Cu, Co, Cr, In, and Ni, particularly the transition metals for example Au, Pt, Pd, Cu, Cr, Ni, and mixtures thereof. Exemplary metal composites are Au—Ag, Ag—Cu, Au—Ag—Cu, and Au—Ag—Pd. Suitable non-metals in the metal composite include for example Si, C, and Ge. The various components of the silver composite may be present in an amount ranging for example from about 0.01% to about 99.9% by weight, particularly from about 10% to about 90% by weight. In embodiments, the silver composite is a metal alloy composed of silver and one, two or more other metals, with silver comprising for example at least about 20% of the nanoparticles by weight, particularly greater than about 50% of the nanoparticles by weight. Unless otherwise noted, the weight percentages recited herein for the components of the silver-containing nanoparticles do not include any stabilizer.

Silver nanoparticles composed of a silver composite can be made for example by using a mixture of (i) a silver compound (or compounds, especially silver (I) ion-containing compounds) and (ii) another metal salt (or salts) or another non-metal (or non-metals) during the reduction step.

Those skilled in the art will appreciate that metals other than silver may be useful and can be prepared in accordance with the methods disclosed herein. Thus, for example, nanocomposites may be prepared with nanoparticles of copper, gold, palladium, or composites of such exemplary metals.

In embodiments, the nanocomposites accessible by the methods herein may be used in conjunction with complex nanostructured materials that also include, without limitation, carbon nanotubes (CNTs, including single-walled, double-walled, and multi-walled), graphene sheet, nanoribbons, nano-onions, hollow nanoshell metals, nano-wires and the like. In embodiments, CNTs may be added in amounts that enhance electrical and thermal conductivity.

In embodiments, the plurality of silver nanoparticles have an effective diameter in a range from about 1 nm to about 500 nm, or about 25 nm to about 100 nm, or about 25 nm to about 50 nm.

In embodiments, the plurality of nanoparticles are present in an amount from about 0.005 weight percent to about 10 weight percent of the total shell weight, such as from about 0.005 weight percent to about 1 weight percent, or about 1 weight percent to about 5 weight percent, or about 5 weight percent to about 10 weight percent, including any range in between or overlapping ranges. In embodiments, the plurality of nanoparticles may be present in an amount greater than 10 weight percent of the total shell weight, such as about 15 weight percent, or about 20 weight percent, or about 30 weight percent, including any value in between and fractions thereof.

In embodiments, the nanocomposite is disposed in a coating. In embodiments, the coating comprises substantially the nanocomposite material. In other embodiments, the coating may comprise a further matrix material, such as a polymer matrix which may be any thermoset or any thermoplastic resin. In embodiments, other additives may be included in accordance with intended downstream application including, without limitation additional biocidal additives (e.g., bactericide, fungicide and algicide), UV protection additives, and/or flame retardant additives.

In embodiments, the nanocomposite may be present as a portion of a device as part of a sensor or for antimicrobial applications. In embodiments, the nanocomposite may be provided as printable particles and may function as part of a device as a substrate. For example, a printed nanocomposite may function as pH paper colorimetric strip. The nanocomposite can also be used in solution where testing components can include core-shell latex solutions having reagents for conducting a detection assay which comprises noble metal nanoparticles conjugated to ligands specific for a target entity which is coated onto a latex particle.

The nanoparticle composite in a shell or coating of particles may be conjugated to ligands specific for target entities. The ligands are used to detect that entity. The aggregation of the metal nanoparticles may cause a color shift in the solution or on the substrate. This colorimetric detection assay or sensor is based on the principles that noble metal nanoparticles can aggregate at least as close as the diameter of the nanoparticles and resonate at a different plasmonic resonance frequency than unbound nanoparticles, non-aggregated nanoparticles of the same size and material. Thus, using nanoparticles tagged with ligand specific for binding the target entity (or a component of a target entity) can facilitate detection of the target entity. A color shift occurs in the solution when the nanoparticle conjugates come together in close proximity and form a clump. The color shift indicates the presence of the target entity in the sample. Nanoparticles in close proximity with each other reflect a different frequency of visible light than the non-aggregated metal nanoparticles reflect. If there is no color shift, the metal nanoparticle ligand conjugate remains unbound to any target and therefore the biological, environmental or "test" sample is negative for the target entity.

In embodiments, the nanocomposites herein are incorporated in an aqueous ink, a dry ink, a 3-dimensional or additive composite ink, or a gravure ink. In embodiments, the nanocomposite is incorporated in an ink suitable for flexography, offset printing or offset lithography.

In embodiments, there are provided methods of making a core-shell nanocomposite comprising: heating a sulfonated polyester resin in water at a temperature from about 65° C.

to 90° C.; adding aqueous solution of silver (I) ion source dropwise to the heated sulfonated polyester form an emulsion; optionally adding an aqueous solution of a reducing agent dropwise to emulsion; and adding the emulsion dropwise to polystyrene-co-n-butyl acrylate latex nanoparticles in water, continuing heating to form the core-shell nanocomposite. In embodiments, the nanocomposite has an effective diameter in a range from about 50 nm to about 500 nm.

In embodiments, the sulfonated polyester is branched.

In embodiments, the sulfonated polyester is a sodium, potassium or lithium salt of a polymer selected from the group consisting of poly(1,2-propylene-5-sulfoisophthalate), poly(neopentylene-5-sulfoisophthalate), poly(diethylene-5-sulfoisophthalate), copoly-(1,2-propylene-5-sulfoisophthalate)-copoly-(1,2-propylene-terephthalatephthalate), copoly-(1,2 propylenediethylene5-sulfoisophthalate)-copoly-(1,2-propylene-diethylene-terephthalatephthalate) copoly(ethylene neopentylene-5-sulfoiso-phthalate)-copoly(ethylene-neopentylene-terephthalatephthalate), and copoly(propoxylated bisphenol A)-copoly-(propoxylated bisphenol A-5-sulfoisophthalate).

In embodiments, the plurality of silver nanoparticles have an effective diameter in a range from about 1 nm to about 500 nm, or about 25 nm to about 100 nm, or about 25 nm to about 50 nm.

In embodiments, there are provided articles comprising the nanocomposites described herein. In embodiments, the article is a coating, a sensor, or an ink. In particular, inks may include build inks for 3-printing, aqueous inks, and the like. The nanocomposites can be applied to a substrate of choice including, for example, textiles (canvas, jute, polyesters, cotton, polyester-cotton mix and non-woven fabric), foil, any variety of paper (lightweight, heavyweight, coated, uncoated, paperboard, cardboard, etc.), plastic (polycarb, acrylic, plexiglass, polyester, polyethylene, etc.), foam board, aluminum composite materials.

The following Examples are being submitted to illustrate embodiments of the present disclosure. These Examples are intended to be illustrative only and are not intended to limit the scope of the present disclosure. Also, parts and percentages are by weight unless otherwise indicated. As used herein, "room temperature" refers to a temperature of from about 20° C. to about 25° C.

EXAMPLES

Example 1 (Comparative Example, Preparation of Branched Sulfonated Amorphous Polyesters (BSPE-1))

A branched amorphous sulfonated polyester resin comprised of 0.425 mole equivalent of terephthalate, 0.080 mole equivalent of sodium 5-sulfoisophthalic acid, 0.4501 mole equivalent of 1,2-propanediol, and 0.050 mole equivalent of diethylene glycol, was prepared as follows. In a one-liter Parr reactor equipped with a heated bottom drain valve, high viscosity double turbine agitator, and distillation receiver with a cold water condenser was charged 388 grams of dimethylterephthalate, 104.6 grams of sodium 5-sulfoisophthalic acid, 322.6 grams of 1,2-propanediol (1 mole excess of glycols), 48.98 grams of diethylene glycol, (1 mole excess of glycols), trimethylolpropane (5 grams) and 0.8 grams of butyltin hydroxide oxide as the catalyst. The reactor was heated to 165° C. with stirring for 3 hours and then again heated to 190° C. over a one hour period, after which the pressure was slowly reduced from atmospheric pressure to about 260 Torr over a one hour period, and then reduced to 5 Torr over a two hour period. The pressure was then further reduced to about 1 Torr over a 30 minute period and the polymer was discharged through the bottom drain onto a container cooled with dry ice to yield 460 grams of sulfonated-polyester resin. The branched sulfonated-polyester resin had a glass transition temperature measured to be 54.5° C. (onset) and a softening point of 154° C.

Example 2 (Control, BSPE, No Ag)

The reaction was carried out in a 3 necked, 500 mL round bottom flask equipped with an overhead stirrer, reflux condenser, thermocouple, hot plate, and nitrogen entrance (the condenser acted as the nitrogen exit). 125 mL of deionized water was charged into flask at room temperature (22° C.). The water was heated to 90° C. with stirring while nitrogen running through the solution (RPM=330). Then 50.0 g of finely ground, solid BSPE-1 was added to the deionized water (DIW) (RPM=400). The solution was stirred at 90° C. for 2 hours (RPM=400). Then the BSPE emulsion was cooled to room temperature with stirring (RPM=400). The final appearance was a white, opaque solution.

Example 3 (Lab Scale Control, Poly(Styrene-Co-n-Butyl Acrylate Latex Control, No Ag)

A latex emulsion comprised of polymer particles generated from the emulsion polymerization of styrene, n-butyl acrylate, and beta-carboxyethyl acrylate (βCEA) was prepared as follows.

A surfactant solution of 6.9 grams Dowfax 2A1 (anionic alkyldiphenyloxide disulfonate surfactant; The Dow Chemical Company) and 306.7 grams de-ionized water was prepared by mixing for 10 minutes in a stainless steel holding tank. The holding tank was then purged with nitrogen for 5 minutes before transferring into the reactor. The reactor was then continuously purged with nitrogen while being stirred at 450 rpm. The reactor was then heated up to 80° C. at a controlled rate, and held there. Separately, 7.1 grams of ammonium persulfate initiator was dissolved in 48.9 grams of de-ionized water.

Separately, the monomer emulsion was prepared in the following manner. 264.9 g of styrene, 88.3 g of butyl acrylate, 10.6 g of beta-CEA and 1.6 g of 1-dodecanethiol (DDT) were added to a premix of 0.6 g of Dowfax 2A1 in 164.32 g of deionized water were mixed to form an emulsion. 2% of the above emulsion (10.6 g) was then slowly dropped into the reactor containing the aqueous surfactant phase at 80° C. to form the "seeds" while being purged with nitrogen. The initiator solution was then slowly charged into the reactor. The monomer emulsion was fed into the reactor at 2.0 g/min. Once all the monomer emulsion was charged into the main reactor, the temperature was held at 80° C. for an additional 3 hours to complete the reaction. Full cooling was then applied and the reactor temperature was reduced to 25° C. The product was collected into a holding tank and sieved with a 25 μm screen.

The particle size was then measured by Nanotrac® U2275E particle size analyzer to have a D50 of 220 nm.

Example 4 (Control, Styrene-Acrylate+BSPE (No Ag))

The reaction was carried out in a 3 necked, 500 mL round bottom flask equipped with an overhead stirrer, reflux condenser, thermocouple, hot plate, and nitrogen entrance (the condenser acted as the nitrogen exit). 50.00 g of deionized water and 50.00 g EP08 (an emulsion polymerized latex, poly(styrene-co-n-butyl acrylate) was charged into the flask at room temperature (22° C.). The hot plate was set to 60° C. and nitrogen was run through the system (RPM=250). Once the temperature had stabilized, a mixture of 3.57 g BSPE stock solution (25.65% solid) and 46.43 g deionized water were added dropwise at a rate of approximately 1 drop/second. After the solution had been added, the mixture was mixed at 60° C. for 1.5 hours. The solution was allowed to cool to room temperature (RPM=250). The final appearance was a white, opaque solution.

Example 5 (Precursor to Final Composite; BSPE-Ag)

The reaction was carried out in a 3 necked, 500 mL round bottom flask equipped with an overhead stirrer, reflux condenser, thermocouple, hot plate, and nitrogen entrance (the condenser acted as the nitrogen exit). 240 mL of deionized water was charged into the flask at room temperature (22° C.). The hot plate was set to 90° C. and nitrogen was run through the system (RPM=300). Once the temperature had stabilized, 5.95 g of solid BSPE-1 was added to the system in a finely ground state (RPM=300). The solution became hazy and had a blue tinge. After 0.5 hrs, 0.0768 g AgNO3 dissolved in 5 mL deionized water was added dropwise to the solution at a rate of approximately 1 drop/second (RPM=300). The solution became slightly darker (brownish). After 0.5 hrs, 5 mL of 1% (w/w %) trisodium citrate solution (reducing agent) was added to the system dropwise at a rate of 1 drop/second. Upon completion, the solution was stirred at 90° C. for 2 hours (RPM=300). The solution was allowed to cool to room temperature (RPM=300). The final appearance was a peach coloured, slightly hazy solution.

Example 6 (Styrene-Acrylate Coated with Pre-Made Solution of BSPE-Ag(0))

Solution A: Example 5
Solution B: The reaction was carried out in a 3 necked, 500 mL round bottom flask equipped with an overhead stirrer, reflux condenser, thermocouple, hot plate, and nitrogen entrance (the condenser acted as the nitrogen exit). 50.00 g of EP08 (an emulsion polymerized latex, poly (styrene-co-n-butyl acrylate) and 50.00 g of deionized water were charged into the flask at room temperature (22° C.). The hot plate was set to 60° C. and nitrogen was run through the system (RPM=250). 50.00 g of solution A was then added to the flask dropwise at approximately 1 drop/second. After solution A had been added, the mixture was mixed at 60° C. for 2.5 hours. The solution was allowed to cool to room temperature (RPM=250). The final appearance was a white, opaque solution.

TABLE 1

Particle characterization results for composites and final core-shell EA latex particles coated with BSPE/AgNPs

| Example # | Reducing Agent Used | Theoretical % Solids | Loading [AgNO$_3$] (M) | Loading [AgNO$_3$] (w/w %) | Actual Solids (%) | Particle Size D50 (nm) | Zeta Potential (mV) | Zeta Deviation (mV) | Appearance* |
|---|---|---|---|---|---|---|---|---|---|
| 2 | None | 28.57% | None | None | 29.46% | 31.8 | −62.7 | 11.90 | White solution |
| 3 | None | 40.88% | None | None | 40.88% | 183.2 | −68.5 | 9.74 | White solution |
| 4 | None | 14.24% | None | none | 14.29% | 150.9 | −49.5 | 7.26 | White solution |
| 5 | TSC | 2.37% | 1.81E−03 | 0.03% | 2.44% | 27.4 | −61.9 | 17.00 | Stable, translucent brown solution |
| 6 | TSC | 14.44% | 5.89E−04 | 0.01% | 14.20% | 191.8 | −60.3 | 8.21 | Stable, white opaque solution |

*observations approximately 3 weeks after synthesis.

TABLE 2

Particle characterization results for composites and final core-shell EA latex particles coated with BSPE/AgNPs

| Example # | GPC - molecular weight (×1000) | GPC - molecular number (×1000) | Polydispersity (PD) | DSC 2$^{nd}$ onset Tg (° C.) | DSC 2$^{nd}$ midpoint Tg (° C.) | DSC 2$^{nd}$ offset Tg (° C.) | Description of sample |
|---|---|---|---|---|---|---|---|
| 2 | 54.81 | 23.23 | 2.35 | 55.70 | 59.19 | 62.69 | St/Ac* latex |
| 3 | 4.226 | 1.76 | 2.40 | 55.09 | 59.31 | 63.52 | BSPE |
| 4 | 32.99 | 9.47 | 3.48 | 55.38 | 59.87 | 64.37 | St/Ac + BSPE (no Ag) - control |
| 5 | 5.131 | 2.22 | 2.31 | 54.62 | 58.32 | 62.03 | BSPE-Ag (used in the formulation of Ex. 6) |
| 6 | 57.83 | 22.64 | 2.55 | 53.16 | 59.90 | 63.63 | St/Ac latex coated with pre-made solution of BSPE-Ag(0) |

*styrene-acrylate

Table 2 shows the molecular weight (Mw) and molecular number (Mn) distribution as well as the polydispersity of the separate compositions used to synthesize the core-shell hybrid composite as well as the core-shell metal organic particles themselves. The Mw of Example 6, core-shell metal/organic composite shows a slight increase in molecular weight due to the layering of the styrene-acrylate latex with the BSPE/AgNP shell. While the differential scanning calorimeter (DSC) data shows a marginal decrease in glass transition due to the BSPE/AgNP shell slightly plasticizing the styrene-acrylate core at the interface between the two very different organic composites.

What is claimed is:

1. A method of making a core-shell nanocomposite, wherein the core-shell nanocomposite comprises a core, a shell disposed about the core, and a plurality of silver nanoparticles;

the method comprising:
heating a sulfonated polyester resin in water at a temperature from about 65° C. to about 90° C.;
adding an aqueous solution of silver (I) ion source dropwise to the heated sulfonated polyester to effect the reduction of silver (I) ion to silver (0) to form the plurality of silver nanoparticles in situ and form an emulsion;
optionally adding an aqueous solution of a reducing agent dropwise to the emulsion;
adding the emulsion dropwise to polystyrene-co-n-butyl acrylate latex nanoparticles in water, continuing heating to form the shell disposed about the core comprising the polystyrene-co-n-butyl acrylate latex nanoparticles, thereby forming the core-shell nanocomposite;
wherein the plurality of silver nanoparticles are present in an amount from 0.005 weight percent to 10 weight percent of the total shell weight.

2. The method of claim 1, wherein the nanocomposite has an effective diameter in a range from about 25 nm to about 500 nm.

3. The method of claim 1, wherein the sulfonated polyester is branched.

4. The method of claim 1, wherein the sulfonated polyester is a sodium, potassium or lithium salt of a polymer selected from the group consisting of poly(1,2-propylene-5-sulfoisophthalate), poly(neopentylene-5-sulfoisophthalate), poly(diethylene-5-sulfoisophthalate), copoly-(1,2-propylene-5-sulfoisophthalate)-copoly-(1,2-propylene-terephthalate phthalate), copoly-(1,2 propylenediethylene-5-sulfoisophthalate)-copoly-(1,2-propylene-diethylene-terephthalate phthalate), copoly(ethylene neopentylene-5-sulfoisophthalate)-copoly(ethylene-neopentylene-terephthalate phthalate), and copoly(propoxylated bisphenol A)-copoly-(propoxylated bisphenol A-5-sulfoisophthalate).

5. A method of making a core-shell nanocomposite, wherein the core-shell nanocomposite comprises a core, a shell disposed about the core, and a plurality of silver nanoparticles;

the method comprising:
heating a sulfonated polyester resin in water at a temperature from about 65° C. to about 90° C.;
adding an aqueous solution of silver (I) ion source dropwise to the heated sulfonated polyester to effect the reduction of silver (I) ion to silver (0) to form the plurality of silver nanoparticles in situ and form an emulsion;
optionally adding an aqueous solution of a reducing agent dropwise to the emulsion;
adding the emulsion dropwise to polystyrene-co-n-butyl acrylate latex nanoparticles in water, continuing heating to form the shell disposed about the core comprising the polystyrene-co-n-butyl acrylate latex nanoparticles, thereby forming the core-shell nanocomposite;
wherein the plurality of silver nanoparticles are present in an amount from greater than 10 weight percent of to 30 the total shell weight.

* * * * *